United States Patent
Hwang et al.

(10) Patent No.: US 9,956,157 B2
(45) Date of Patent: May 1, 2018

(54) COMPOSITION CONTAINING FUCOSTEROL FOR SKIN WHITENING OR MOISTURIZING

(71) Applicant: INDUSTRY-ACADEMIC COOPERATION FOUNDATION, YONSEI UNIVERSITY, Seoul (KR)

(72) Inventors: Jae Kwan Hwang, Seoul (KR); Seon Wook Woo, Seoul (KR); Chang Hee Kim, Seoul (KR); Mi Bo Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days. days.

(21) Appl. No.: 15/113,692

(22) PCT Filed: Jan. 23, 2015

(86) PCT No.: PCT/KR2015/000727
§ 371 (c)(1),
(2) Date: Jul. 22, 2016

(87) PCT Pub. No.: WO2015/111953
PCT Pub. Date: Jul. 30, 2015

(65) Prior Publication Data
US 2017/0000714 A1   Jan. 5, 2017

(30) Foreign Application Priority Data

Jan. 23, 2014  (KR) ......................... 10-2014-0008415
Jan. 23, 2014  (KR) ......................... 10-2014-0008430

(51) Int. Cl.
*A61K 8/63* (2006.01)
*A61Q 19/00* (2006.01)
(Continued)

(52) U.S. Cl.
CPC .............. *A61K 8/63* (2013.01); *A23L 33/105* (2016.08); *A23L 33/11* (2016.08); *A61K 8/0216* (2013.01);
(Continued)

(58) Field of Classification Search
CPC ....................................................... A62K 8/63
See application file for complete search history.

(56) References Cited

U.S. PATENT DOCUMENTS

2006/0272105 A1*  12/2006  Molenda .................. A61Q 5/02
8/405

FOREIGN PATENT DOCUMENTS

KR   10-2004-0108534 A   12/2004
KR   10-2013-0136048 A   12/2013
(Continued)

OTHER PUBLICATIONS

Hwang et al (Mar Biotechnol (2014) 16:361-370.*
(Continued)

*Primary Examiner* — Benjamin Packard
(74) *Attorney, Agent, or Firm* — Sughrue Mion, PLLC

(57) ABSTRACT

The present invention relates to a novel use of fucosterol and, more specifically, to a composition for skin whitening or composition for skin moisturizing, which is characterized by containing fucosterol. Fucosterol of chemical formula 1 below has an excellent whitening effect of inhibiting melanin generation and tyrosinase activity, and thus can be used as an active ingredient of a cosmetic composition for whitening, a food composition, or a pharmaceutical composition. Furthermore, the fucosterol of chemical formula 1 below has an excellent moisturizing function by forming dead skin cell membranes, promoting the differentiation of dead skin cells, and generating natural moisturization factors, and thus can
(Continued)

be used as an active ingredient of a cosmetic composition for moisturizing, a food composition, or a pharmaceutical composition

[Chemical Formula 1]

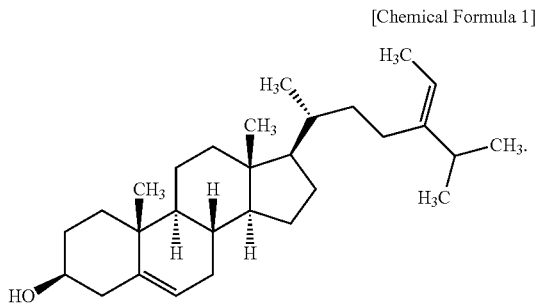

8 Claims, 12 Drawing Sheets

(51) Int. Cl.
  A61Q 19/02      (2006.01)
  A23L 33/11      (2016.01)
  A61K 8/02       (2006.01)
  A61K 31/575     (2006.01)
  A23L 33/105     (2016.01)
  A61K 9/00       (2006.01)
  A61K 9/20       (2006.01)
  A61K 9/48       (2006.01)

(52) U.S. Cl.
  CPC .......... *A61K 9/0014* (2013.01); *A61K 9/0019* (2013.01); *A61K 9/2054* (2013.01); *A61K 9/4866* (2013.01); *A61K 31/575* (2013.01); *A61Q 19/00* (2013.01); *A61Q 19/007* (2013.01); *A61Q 19/02* (2013.01); *A23V 2002/00* (2013.01); *A61K 2800/74* (2013.01)

(56) References Cited

FOREIGN PATENT DOCUMENTS

KR    10-2013-0136053 A    12/2013
WO       2013-184884 A1    12/2013

OTHER PUBLICATIONS

Hwang et al (Mar Biotechnol (2014) 16:361-370 Article Information at http://link.springer.com/article/10.1007/s10126-013-9554-8, downloaded Nov. 28, 2016.*

Sanchez-Machado et al (Biomed. Chromatogr. 18: 183-190 (2004)).*
International Searching Authority, International Search Report of PCT/KR2015/000727 dated Apr. 29, 2015.
Jonathan L. Rees, "Genetics of Hair and Skin Color", Annu. Rev. Genet., 2003, pp. 67-90, vol. 37.
William H. Tolleson, "Human Melanocyte Biology, Toxicology, and Pathology", Journal of Environmental Science and Health, Part C, 2005, pp. 105-161, vol. 23, No. 2.
Gertrude-E. Costin et al., "Human skin pigmentation: melanocytes modulate skin color in response to stress", The FASEB Journal, 2007, pp. 976-994, vol. 21, No. 4.
Zoe Diana Draelos, "Skin lightening preparations and the hydroquinone controversy", Dermatologic Therapy, 2007, pp. 308-313, vol. 20, No. 5.
Jeong Kee Kim et al. "Beneficial Effect of a Collagen Peptide Supplement on the Epidermal Skin Barrier", Korean J. Food Sci. Technol., 2011, pp. 458-463, vol. 43, No. 4.
Eleonora Candi et al., "The Cornified Envelope: A Model of Cell Death in the Skin", Nature Reviews Molecular Cell Biology, 2005, pp. 328-340, vol. 6, Nol. 4.
Aileen Sandilands et al. "Filaggrin in the frontline: role in skin barrier function and disease", Journal of Cell Science, 2009, pp. 1285-1294, vol. 122.
Mahnaz Khanavi et al., "Cytotoxicity of fucosterol containing fraction of marine algae against breast and colon carcinoma cell line", 2012, pp. 60-64, vol. 8, No. 29.
Yeon Sil Lee et al., "Anti-Diabetic Activities of Fucosterol from Pelvetia siliquosa", Archives of Pharmacal Research, 2004, pp. 1120-1122, vol. 27, No. 11.
Tomohiro Nabekura et al., "Effects of plant sterols on human multidrug transporters ABCB1 and ABCC1", 2008, pp. 363-368, vol. 369, No. 2.
Mohammed-Amine Madoui et al., "Sterol metabolism in the oomycete Aphanomyces euteiches, a legume root pathogen", New Phytologist, 2009, pp. 291-300, vol. 183, No. 2.
Yong Li et al., "Chemical components and its antioxidant properties in vitro: An edible marine brown alga, *Ecklonia cava*", Bioorg Med Chem., 2009, pp. 1963-1974, vol. 17, No. 5 (Abstract).
M. Plaza et al., "Screening for bioactive compounds from algae", Journal of Pharmaceutical and Biomedical Analysis, 2010, pp. 450-455, vol. 51, No. 2.
S. Sadish Kumar et al., "New antifungal steroids from Turbinaria conoides (J. Agardh) Kutzing", 2010, pp. 1481-1487, vol. 24, No. 15.
Myung-Suk Kim et al., "Fucosterol Inhibits Matrix Metalloproteinase Expression and Promotes Type-1 Procollagen Production in UVB-induced HaCaT Cells", Photochemistry and Photobiology, 2013, pp. 911-918, vol. 89.
Gupta, Shilpi et al., "Bioactive potential and possible health effects of edible brown seaweeds", Trends in Food Science & Technology, 2011, pp. 315-326, vol. 22, No. 6.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 1
accacagtcc atgccatcac                                          20

<210> SEQ ID NO 2
<211> LENGTH: 20
<212> TYPE: DNA
<213> ORGANISM: Artificial Sequence
<220> FEATURE:
<223> OTHER INFORMATION: GAPDH Reverse primer

<400> SEQUENCE: 2
ccacccgagc cacatcgctc                                          20
```

```
<210> SEQ ID NO 3
<211> LENGTH: 19
<212> TYPE: DNA
<213> ORGANISM: Artificial Sequence
<220> FEATURE:
<223> OTHER INFORMATION: MITF Forward primer

<400> SEQUENCE: 3
agtcaacctc tgaagagca                                               19

<210> SEQ ID NO 4
<211> LENGTH: 20
<212> TYPE: DNA
<213> ORGANISM: Artificial Sequence
<220> FEATURE:
<223> OTHER INFORMATION: MITF Reverse primer

<400> SEQUENCE: 4
cgtgttcata cctgggcact                                              20

<210> SEQ ID NO 5
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 5
tgaccttggc caggggtgct                                              20

<210> SEQ ID NO 6
<211> LENGTH: 20
<212> TYPE: DNA
<213> ORGANISM: Artificial Sequence
<220> FEATURE:
<223> OTHER INFORMATION: GAPDH Reverse primer

<400> SEQUENCE: 6
ccacccgagc cacatcgctc                                              20

<210> SEQ ID NO 7
<211> LENGTH: 21
<212> TYPE: DNA
<213> ORGANISM: Artificial Sequence
<220> FEATURE:
<223> OTHER INFORMATION: Loricrin Forward primer

<400> SEQUENCE: 7
gggtaccacg gaggcgaagg a                                            21

<210> SEQ ID NO 8
<211> LENGTH: 21
<212> TYPE: DNA
<213> ORGANISM: Artificial Sequence
<220> FEATURE:
<223> OTHER INFORMATION: Loricrin Reverse primer

<400> SEQUENCE: 8
actgaggcac tggggttggg a                                            21

<210> SEQ ID NO 9
<211> LENGTH: 20
<212> TYPE: DNA
<213> ORGANISM: Artificial Sequence
<220> FEATURE:
<223> OTHER INFORMATION: Involucrin Forward primer
```

```
<400> SEQUENCE: 9
ggggcagctg aagcacctgg                                              20

<210> SEQ ID NO 10
<211> LENGTH: 20
<212> TYPE: DNA
<213> ORGANISM: Artificial Sequence
<220> FEATURE:
<223> OTHER INFORMATION: Involucrin Reverse primer

<400> SEQUENCE: 10
gagacgggcc acctagcgga                                              20

<210> SEQ ID NO 11
<211> LENGTH: 20
<212> TYPE: DNA
<213> ORGANISM: Artificial Sequence
<220> FEATURE:
<223> OTHER INFORMATION: Transglutaminase Forward primer

<400> SEQUENCE: 11
cttccgtctg cgcaccccag                                              20

<210> SEQ ID NO 12
<211> LENGTH: 20
<212> TYPE: DNA
<213> ORGANISM: Artificial Sequence
<220> FEATURE:
<223> OTHER INFORMATION: Transglutaminase Reverse primer

<400> SEQUENCE: 12
aggcacaaac gactggcgca                                              20

<210> SEQ ID NO 13
<211> LENGTH: 21
<212> TYPE: DNA
<213> ORGANISM: Artificial Sequence
<220> FEATURE:
<223> OTHER INFORMATION: Filaggrin Forward primer

<400> SEQUENCE: 13
agtgcactca gggggctcac a                                            21

<210> SEQ ID NO 14
<211> LENGTH: 20
<212> TYPE: DNA
<213> ORGANISM: Artificial Sequence
<220> FEATURE:
<223> OTHER INFORMATION: Filaggrin Reverse primer

<400> SEQUENCE: 14
ccggcttggc cgtaatgtgt                                              20

<210> SEQ ID NO 15
<211> LENGTH: 20
<212> TYPE: DNA
<213> ORGANISM: Artificial Sequence
<220> FEATURE:
<223> OTHER INFORMATION: Caspase 14 Forward primer

<400> SEQUENCE: 15
cgggactcac aaccaaagga                                              20

<210> SEQ ID NO 16
<211> LENGTH: 20
```

```
<212> TYPE: DNA
<213> ORGANISM: Artificial Sequence
<220> FEATURE:
<223> OTHER INFORMATION: Caspase 14 Reverse primer

<400> SEQUENCE: 16
gggtcccttt gttctcctcg                                              20
```

1

COMPOSITION CONTAINING FUCOSTEROL FOR SKIN WHITENING OR MOISTURIZING

CROSS REFERENCE TO RELATED APPLICATIONS

This application is a National Stage of International Application No. PCT/KR2015/000727 filed Jan. 23, 2015, claiming priority based on Korean Patent Application Nos. 10-2014-0008415 filed Jan. 23, 2014, and 10-2014-0008430 filed Jan. 23, 2014, the contents of which are incorporated herein by reference in their entirety.

TECHNICAL FIELD

The present invention is achieved by Project NO: D10906112H320000170 under the support of the Korea Ministry of Maritime Affairs and Fisheries, and the research management agency of the project is the Korea Ocean Research and Development Institute, the research business name is "development of abroad marine organism resources and establishment of application foundation", the research project name is "securement of marine bio-resources in Indonesia and analysis of basic bioactivity", the research managing department is the Industry-Academic Cooperation Foundation, YONSEI University, and the research period is Nov. 1, 2009 to Jun. 30, 2012.

The present invention relates to a novel use of fucosterol, and more specifically, to a composition for skin whitening or moisturizing, which is characterized by including fucosterol.

BACKGROUND ART

A person's skin color is determined by many factors, such as the activity of melanocytes to make melanin pigment, distribution of blood vessel, thicknesses of skin, whether pigments such as carotenoid and hemoglobin, and the like are present inside and outside of the human body. Physiological factors related to genetic factors, secretion of hormone, stress, and the like and environmental factors such as UV irradiation have an effort on formation of the melanin pigment (Annu. Rev. Genet. 37:67-90, 2003).

A thing having a significant effect on a generation mechanism of the melanin is an enzyme called tyrosinase and the tyrosinase is involved in the oxidation of tyrosine in a melanosome in the melanocyte. The tyrosinase is activated by UV exposure to be applied to tyrosine to synthesize a melanin polymer by an oxidation process of generating 3,4-dihydroxyphenylalanine (DOPA) and DOPAquinone (J. Environ. Sci. Health. 23 (2): 105-161, 2005).

The melanin is present in an epidermal layer of the outside of the skin and serves to protect skin organs below the dermis from UV and the like and capture free radicals generated in the skin of the body to protect proteins and genes in the skin. However, it is known that when the melanin is over-produced, the melanin forms melasma, freckles, and the like and promotes skin aging, and plays an important role in causing skin cancer (FASEB J. 21(4): 976-994, 2007).

In order to treat or reduce skin dyspigmentation symptoms such as melasma, freckles, and pigmentation and excessive melanin pigmentation generated by UV exposure and the like, ascorbic acid, kojic acid, arbutin, hydroquinone, glutathione, or derivatives thereof, and materials having a tyrosinase-inhibiting activity are combined in cosmetics or medicines and have been used from before. However, the use of these materials is limited due to an insufficient whitening effect, a safety problem for the skin, formulation during combination of the cosmetic, and a stability problem (Dermatol. Ther. 20(5):308-313, 2007). Accordingly, in order to solve the problem of the active ingredients, the demand for the active ingredient derived from a natural material with proven safety and stability is proposed.

The stratum corneum of the skin is present in an outermost layer in the skin and directly in contact with an external environment to serve as an important barrier function to protect the body from external physical and chemical stresses. The barrier function is maintained by homeostasis of the epidermis. The epidermis homeostasis maintains the persistent skin barrier function by forming a skin barrier called a stratum corneum via terminal differentiation through a differentiation process according to growing division and cell migration of keratinocytes of a base layer (Korean J. Food. Sci. Technol. 43:458-463, 2011).

As the keratinocytes are differentiated, two factors affecting moisturizing are generated. First, while the keratinocytes are differentiated, the cell membrane thereof is replaced with a structure called a cornified envelope. The cornified envelope is a membrane structure in which many structural proteins including loricrin, involucrin, and filaggrin are cross-linked by an enzyme which is referred to as transglutaminases to provide a skin protection function for an external environment and suppress water evaporation in the corneous cells (Nat. Rev. Mol. Cell Biol. 6(4):328-340, 2005). The cornified envelope structural protein and the transglutaminases start to be expressed according to the differentiation of the keratinocytes to be used as differentiation markers (Nat. Rev. Mol. Cell Biol. 6(4):328-340, 2005). Therefore, the cornified envelope and the differentiation markers are used as a moisturizing index.

Further, during the differentiation process of the corneous cells, the keratinocytes generate natural moisturizing factors (NMF) to have a function as a skin barrier. A protein which is an important source for generating the NMFs is filaggrin and the filaggrin is decomposed to hydrophilic amino acids by caspase 14 to form the NMFs. The NMFs provide water holding capacity and moisture absorption in the air to functions to maintain the moisturizing ability in the skin (J. Cell Sci. 122:1285-1294, 2009). Accordingly, the maintaining of the NMFs in the skin at an appropriate level is a very important factor in skin health through the skin barrier function.

Fucosterol is a material which is largely included in algae and frequently discovered in algae inhabited on the coast in Asia including Korea, China, Japan, and the like. Until now, it is reported that the activity of the fucosterol includes anti-cancer (Pharmacogn. Mag. 8 (29): 60-64, 2012), anti-diabetic (Arch. Pharm. Res. 27 (11): 1120-1122, 2004), antioxidation (Bioorg. Med. Chem. 17 (5): 1963-1973, 2009), improved blood lipid ingredients (Biochem. Biophys. Res. Commun. 369 (2): 363-368, 2008), improved cholesterol metabolisms (New Phytol. 183 (2): 291-300, 2009), antimicrobial (J. Pharm. Biomed. Anal. 51 (2): 450-4555, 2010), antifungal (Nat. Prod. Res. 24(15): 1481-1487, 2010), anti-aging (Photochem. Photobiol. 89(4): 911-918, 2013), and the like. However, the skin whitening activity and the moisturizing activity of the fucosterol are not reported until now.

Throughout the specification, theses and patent documents are referenced and the citation thereof is represented. The disclosed contents of the cited theses and patent documents are entirely inserted with reference to the specification and thus, a level in the art and the contents of the present invention will be more clearly described.

DISCLOSURE

Technical Problem

The inventors of the present invention investigated that fucosterol included in algae had excellent whitening activity and an excellent moisturizing function while searching materials having the whitening activity or the moisturizing function derived from natural substances, thereby completing the present invention.

Therefore, an object of the present invention is to provide a cosmetic composition for whitening, which is characterized by including fucosterol represented by the following Chemical Formula 1.

[Chemical Formula 1]

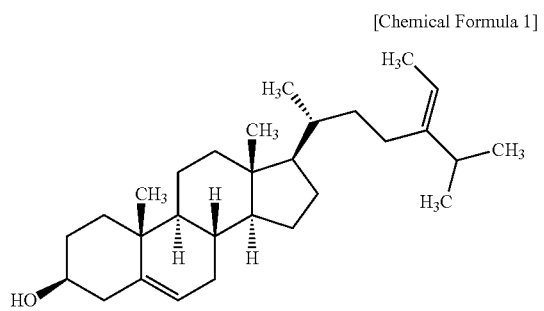

Another object of the present invention is to provide a food composition for whitening, which is characterized by including fucosterol represented by the following Chemical Formula 1.

Yet another object of the present invention is to provide a pharmaceutical composition for whitening, which is characterized by including fucosterol represented by the following Chemical Formula 1.

Still another object of the present invention is to provide a cosmetic composition for moisturizing, which is characterized by including fucosterol represented by the following Chemical Formula 1.

Still yet object of the present invention is to provide a food composition for moisturizing, which is characterized by including fucosterol represented by the following Chemical Formula 1.

Still yet another object of the present invention is to provide a pharmaceutical composition for moisturizing, which is characterized by including fucosterol represented by the following Chemical Formula 1.

Other objects and advantages of the present invention are clearer by the detailed description of the invention, claims, and drawings.

Technical Solution

The present invention relates to a composition for skin whitening which has an excellent whitening efficacy, and more particularly, to cosmetic, food, and pharmaceutical compositions for whitening, which is characterized by including fucosterol represented by the following Chemical Formula 1 as an active ingredient.

According to another aspect of the present invention, the present invention relates to a composition for skin moisturizing, which has an excellent moisturizing function, and more particularly, to cosmetic, food, and pharmaceutical compositions for skin moisturizing, which is characterized by including fucosterol represented by the following Chemical Formula 1 as an active ingredient.

[Chemical Formula 1]

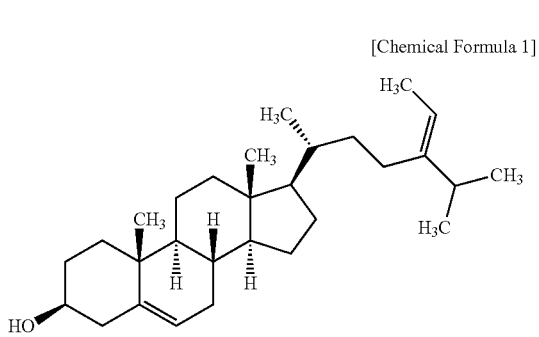

Hereinafter, the contents of the present invention will be described in detail.

In the cosmetic, food, and pharmaceutical compositions for skin whitening or skin moisturizing of the present invention, the fucosterol represented by Chemical Formula 1 may be extracted or isolated from natural raw materials such as algae or synthesized by a chemical synthesis method.

In the compositions of the present invention, the fucosterol may be extracted and isolated from algae including *Silvetia siliquosa, Saccharina japonica, Kjellmaniella crassifolia, Undaria pinnatifida, Cladosiphon okamuranus, Ceratophyllum demersum, Ecklonia cava, Hizikia fusiformis, Eisenia bicyclis, Dictyopteris prolifera, Ishige okamurae, Scytosiphon lomentaria, Colpomenia sinuosa, Sargassum fulvellum, Sargassum coreanum, Sargassum horneri, Sargassum thunbergii, Cystoseira hakodatensis*, and the like.

Further, the fucosterol may be extracted and isolated from plants including *Allium schoenoprasum, Swietenia macrophylla, Corylus avellana, Azadirachta indica, Osmanthus fragrans* var. *aurantiacus, Fructus broussonetiae, Saccharum officinarum, Setaria italica*, and the like.

The fucosterol of the present invention may be extracted from *Silvetia siliquosa* (see [Example 1]).

The isolation and purification of the fucosterol of the present invention may use a column chromatography filling various synthesized resins including silicagel, active alumina, and the like and a high-performance liquid chromatography alone or in combination, but the extraction and purification method is not necessarily limited to the method.

In an exemplary embodiment of the present invention, in order to examine the cytotoxicity of the fucosterol, the fucosterol was treated in B16F10 melanoma cells to measure cell stability through 3-(4,5-dimethylthiazol-2-yl)-2,5-diphenyltetrazolium bromide (MTT) analysis. As a result, the fucosterol of the present invention did not show the toxicity of the B16F10 melanoma cells at a concentration of 0 to 20 µM (see [Example 2]).

In another exemplary embodiment of the present invention, in the B16F10 melanoma cells, the generation of melanin was promoted by an α-melanocyte stimulating hormone (α-MSH) and then the fucosterol of the present invention was administrated to measure whether to suppress the generation of the melanin. As a result, it was verified that the fucosterol of the present invention effectively inhibited the generation of melanin (see [Examples 3 and 4]).

In another exemplary embodiment of the present invention, in the B16F10 melanoma cells, the activity of tyrosinase was increased by the α-MSH and then the fucosterol of the present invention was administrated to measure whether to inhibit the activity of the tyrosinase. As a result, it was verified that the fucosterol of the present invention effectively inhibited the activity of the tyrosinase (see [Example 5]).

In another exemplary embodiment of the present invention, in the B16F10 melanoma cells, the protein expression of the tyrosinase was increased by the α-MSH and then the fucosterol of the present invention was administrated to measure whether to inhibit the protein expression of the tyrosinase. As a result, it was verified that the fucosterol of the present invention effectively inhibited the protein expression of the tyrosinase (see [Example 6]).

In another exemplary embodiment of the present invention, in the B16F10 melanoma cells, the protein expression of TRP-1 (tyrosinase-related protein 1) and TRP-2 (tyrosinase-related protein 2) was increased by the α-MSH and then the fucosterol of the present invention was administrated to measure whether to inhibit the protein expression of the TRP-1 and TRP-2. As a result, it was verified that the fucosterol of the present invention effectively inhibited the protein expression of the TRP-1 and TRP-2 (see [Example 7]).

In another exemplary embodiment of the present invention, in the B16F10 melanoma cells, the protein expression of MITF (microphthalmia transcription factor) was increased by the α-MSH and then the fucosterol of the present invention was administrated to measure whether to inhibit the mRNA expression of the MITF. As a result, it was verified that the fucosterol of the present invention effectively inhibited the mRNA expression of the MITF (see [Example 8]).

Accordingly, the fucosterol has excellent whitening activity to be used an active ingredient of a cosmetic composition, a food composition, or a pharmaceutical composition.

The fucosterol of the present invention promotes the formation of a cornified envelope, promotes the differentiation of corneous cells, and forms a natural moisturizing factor, thereby providing an excellent skin moisturizing efficacy.

In the exemplary embodiment of the present invention, the fucosterol of the present invention was treated in cornified keratinocytes and then whether to form the cornified envelope was measured. As a result, it was verified that the fucosterol of the present invention effectively promoted the formation of the cornified envelope (see [Example 9]).

In another exemplary embodiment of the present invention, in the cornified keratinocytes, the fucosterol of the present invention was treated and whether to increase expression of differentiation factors including loricrin, involucrin, and transglutaminase was measured. As a result, it was verified that the fucosterol of the present invention effectively increased the expression of the differentiation factors related with skin moisturizing, such as loricrin, involucrin, and transglutaminase (see [Example 10] and [Example 11]).

In another exemplary embodiment of the present invention, in the cornified keratinocytes, the fucosterol of the present invention was treated and whether to increase the expression of filaggrin and caspase 14 was measured. As a result, it was verified that the fucosterol of the present invention effectively increased the expression of the filaggrin and the caspase 14 (see [Example 12] and [Example 13]).

Accordingly, the fucosterol has an excellent moisturizing function to be used an active ingredient of a cosmetic composition, a food composition, or a pharmaceutical composition.

The fucosterol may be included as an active ingredient of the cosmetic composition for skin whitening and the cosmetic composition for skin moisturizing of the present invention, and the amount thereof is not particularly limited to an effective amount to achieve the whitening effect or the moisturizing function, but is preferably 0.001 to 10 wt %, and more preferably 0.01 to 5 wt % with respect to the total weight of the entire composition. When the content is less than 0.001 wt %, a desired whitening or moisturizing effect cannot be expected, and when the content is greater than 10 wt %, there is a difficulty in safety or preparation of formulation.

In the cosmetic composition for skin whitening and the cosmetic composition for skin moisturizing which include the fucosterol of the present invention as an active ingredient, the formulation thereof is not particularly limited thereto, and for example, the cosmetic compositions may be formulated by cosmetics including emollients, astringents, nutrition lotion, nourishing cream, massage cream, essence, eye cream, eye essence, cleansing cream, cleansing foam, cleansing water, pack, gel, powder, body lotion, body cream, body oil, body essence, and the like.

Further, the cosmetic composition for skin whitening of the present invention may further include other existing whitening ingredients other than the fucosterol, for example, whitening ingredients such as arbutin and ascorbic acid derivatives in order to increase the whitening effect, and kinds and contents of the existing whitening ingredients are well-known to those skilled in the art.

The cosmetic composition for skin moisturizing of the present invention may further include other existing moisturizing ingredients other than the fucosterol in order to increase the moisturizing function and the kinds and the contents of the existing moisturizing ingredients are well-known to those skilled in the art.

Furthermore, the fucosterol according to the present invention may be provided in a form of food composition for whitening or moisturizing. The food composition of the present invention includes all forms including conventional foods, nutritional supplements, health function foods, food additives, feeds, and the like and is taken by animals including humans or stock. The type of food composition may be prepared in various forms according to a general method which is known in the art.

For example, the conventional foods are not limited thereto, but may be prepared by adding the fucosterol to drinks (including alcoholic beverages), fruits and processed foods thereof (for example, canned fruits, bottled foods, jams, marmalade, and the like), fishes, meats and processed foods thereof (for example, ham, sausage, corn beef, and the like), breads and noodles (for example, udon, soba, ramen, spaghetti, macaroni, and the like), fruit juice, various drinks, cookies, taffy, dairy products (for example, butter, cheese, and the like), edible vegetable oil, margarine, vegetable proteins, retort foods, frozen foods, various seasonings (for example, soybean paste, soy sauce, sauces, and the like), and the like. Further, the nutritional supplements are not limited thereto, but may be prepared by adding the fucosterol to capsules, tablets, pellets, and the like. Further, the health function foods are not limited thereto, but for example, may be taken by liquefaction, granulation, encapsulation, and powdering to prepare and drink the fucosterol itself in forms of teas, juices, and drinks. Further, in order to use the fucosterol in a form of food additives, the fucosterol may be prepared and used in a form of powder or concentrated liquids. Further, the food additives may be prepared in a form of a composition by mixing the fucosterol with known active ingredients having the whitening or moisturizing effect.

The fucosterol may be included as an active ingredient of the food composition of skin whitening and the food composition for skin moisturizing, and the amount is not particularly limited as an effective amount to achieve the whitening effect or the moisturizing function, but preferably 0.01 to 100 wt % with respect to the total weight of the entire composition. The food composition of the present invention may be prepared by mixing the fucosterol with other active ingredients which are known to have the whitening or moisturizing effect.

The fucosterol of the present invention may be used itself or in a form of salt or pharmaceutically acceptable salt. The 'pharmaceutically acceptable' means that when the fucosterol is physiologically acceptable and administrated, generally, allergic reaction or similar reaction thereto is not caused, and the salt is preferably an acidic additional salt formed by pharmaceutically acceptable free acid. The free acid may use organic acid and inorganic acid. The organic acid is not limited thereto, but includes citric acid, acetic acid, lactic acid, tartaric acid, maleic acid, fumaric acid, formic acid, propionic acid, oxalic acid, a trifluoroacetic acid, benzoic acid, gluconic acid, meta sulfonic acid, glycolic acid, succinic acid, 4-toluenesulfonic acid, glutamic acid, and aspartic acid. Further, the inorganic acid is not limited thereto, but includes hydrochloric acid, bromic acid, sulfuric acid, and phosphoric acid.

Meanwhile, the pharmaceutical composition of the present invention may include the fucosterol alone or additionally include one or more pharmaceutically acceptable carriers, excipients, or diluents. As the pharmaceutically acceptable carriers, for example, orally-administered carriers or parenterally-administered carriers may be additionally included. The orally-administered carrier may include lactose, starch, cellulose derivatives, magnesium stearate, stearic acid, and the like. Further, the parenterally-administrated carrier may include water, suitable oil, saline, aqueous glucose, glycol, and the like, and further include a stabilizer, and a preservative. The suitable stabilizer includes an antioxidant such as sodium bisulfite, sodium sulfite, or ascorbic acid. The suitable preservative includes benzalkonium chloride, methyl- or propyl-paraben, and chlorobutanol. Other pharmaceutically acceptable carriers may refer to carriers disclosed in the document below (Remington's Pharmaceutical Sciences, 19th ed., Mack Publishing Company, Easton, Pa., 1995).

The pharmaceutical composition of the present invention may be administrated to mammals including a human by any method. For example, the pharmaceutical composition may be orally or parenterally administrated. The parenterally administrating method is not limited thereto, but the pharmaceutical composition may be administered in intravenous, intramuscular, intraarterial, intramedullary, intrathecal, intracardiac, transdermal, subcutaneous, intraperitoneal, intranasal, intestinal canal, topical, sublingual, or intrarectal.

The pharmaceutical composition of the present invention may be formulated as a preparation for oral administration or parenteral administration according to the administration path described above. In the case of the preparation for oral administration, the composition of the present invention may be formulated as powders, granules, tablets, pills, sugar tablets, capsules, liquids, gels, syrups, slurries, suspensions, and the like by using methods known in the art. For example, the oral preparation is processed with a granule mixture by combining and grinding the active ingredient with a solid excipient and adding a suitable adjuvant to obtain tablets or sugar tablets. An example of the suitable excipient may include a filler, such as sugars including lactose, dextrose, sucrose, sorbitol, mannitol, xylitol, erythritol and maltitol, and the like, starches including corn starch, wheat starch, rice starch, potato starch, and the like, celluloses including cellulose, methyl cellulose, sodium carboxymethyl cellulose, hydroxypropyl methyl cellulose, and the like, gelatin, and polyvinylpyrrolidone. Further, in some cases, cross-linked polyvinylpyrrolidone, agar, alginic acid, sodium alginate, or the like may be added as a disintegrating agent.

Furthermore, the pharmaceutical composition of the present invention may additionally include an anti-coagulant, a lubricant, a wetting agent, a flavoring, an emulsifier, a preservative, and the like. The preparation for parenteral administration may be formulated in forms of injections, creams, lotions, external ointments, oil agents, moisturizers, gels, aerosol, and nasal inhalants by methods known in the art. These formulations are disclosed in the document (Remington's Pharmaceutical Science, 15th Edition, 1975. Mack Publishing Company, Easton, Pa. 18042, Chapter 87; Blaug, Seymour) as the prescription which is generally known in all pharmaceutical chemistries.

The total effective amount of the pharmaceutical composition of the present invention may be administrated to a patient with a single dose, and administrated by a fractionated treatment protocol which is administrated for a long time with a multiple dose. In the pharmaceutical composition of the present invention, the content of active ingredient may vary according to a degree of the disease. During the parenteral administration, the pharmaceutical composition may be administrated with a dose of preferably 0.01 to 50 mg and more preferably 0.1 to 30 mg per 1 kg of the body weight a day based on the fucosterol. In addition, during the oral administration, the pharmaceutical composition may be administrated once or several times with a dose of preferably 0.01 to 100 mg and more preferably 0.1 to 50 mg per 1 kg of the body weight a day based on the fucosterol. However, in the capacity of the fucosterol, the effective dose for the patient is determined by considering various factors, such as patient's age, body weight, health, sex, severity of diseases, diet, and excretion rate as well as an administration route of the pharmaceutical composition and the number of treatment times. Thus, when considering the factors, those skilled in the art may determine an appropriate effective dose of the fucosterol according to a specific use for whitening. The pharmaceutical composition according to the present invention is not particularly limited to the formulation, the administration route, and the administration method so long as showing effects of the present invention.

Advantageous Effects

As described above, the fucosterol of the present invention has an excellent whitening effect by inhibiting melanin generation and tyrosinase activity, and thus can be used as an active ingredient of a cosmetic composition for whitening, a food composition, or a pharmaceutical composition.

Further, the fucosterol of the present invention has an excellent moisturizing function by forming dead skin cell membranes, promoting the differentiation of dead skin cells, and generating natural moisturization factors, and thus can be used as an active ingredient of a cosmetic composition for moisturizing, a food composition, or a pharmaceutical composition.

BEST MODE

Hereinafter, the present invention will be described in detail by the following Examples. However, the following Examples are just provided for illustrative purposes in order to help in the understanding for the present invention and the scope of the present invention is not limited thereto.

In all test results below, the activity analysis was performed repetitively three times or more, and the results were represented by mean±standard deviation. Statistical analysis used an ANOVA analysis method (Scheff test) and when a *P value was equal to or less than 0.05 or a ##P value and **P value was equal to or less than 0.01, the values were determined to be statistically significant.

Example 1 Extraction, Isolation, and Purification of Fucosterol 500 g of dried *Silvetia siliquosa* was grinded by a mixer, and a sample of the grinded *Silvetia siliquosa* was put in n-hexane in four times volume and macerated for 48 hrs at room temperature to be extracted. The extracted sample was filtered with a Whatman No. 2 filter, the filtered extract was concentrated by a vacuum rotary concentrator, and then a solvent component was removed to obtain about 15.0 g of a *Silvetia siliquosa* n-hexane extract. 15 g of n-hexane soluble extract was loaded on a silicagel open column (70-230 mesh, Merck&Co., Whitehouse Station, N.J., USA) and split by using a solvent system of mixing hexane and ethyl acetate. According to the split order, 40 lower fractions were divided with a concentration gradient and then the fucosterol which was a compound represented by the following Chemical Formula 1 was isolated (210 mg) from 10-th to 30-th fractions among the fractions.

[Chemical Formula 1]

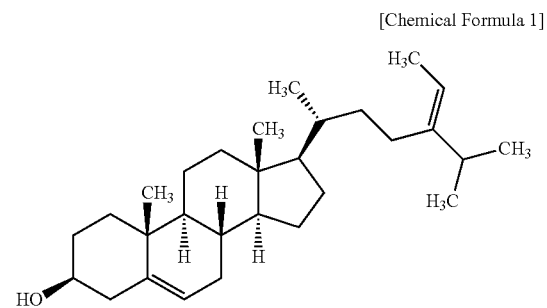

Example 2 Safety Effect According to Fucosterol Treatment in Melanoma Cells

B16F10 melanoma cells were incubated a dulbecco's modified eagle's media (DMEM) medium including 10% fetal bovine serum and then added in a 24-well plate with $2.5 \times 10^4$ cell/mL (the final volume of 1 mL). Fucosterol of 0.1, 1, 5, 10, and 20 μM was treated in the B16F10 melanoma cells, respectively. After treatment of 48 hrs, the medium was removed and a 0.5 mg/mL MTT solution was put in each well by 0.3 mL and the B16F10 melanoma cells were incubated in an incubator for 4 hrs. After 4 hrs, the MTT solution was removed and generated formazan was dissolved by adding dimetyl sulfoxide (DMSO) and then absorbance was measured at 570 nm and the result was illustrated in FIG. 1.

Figure 1:
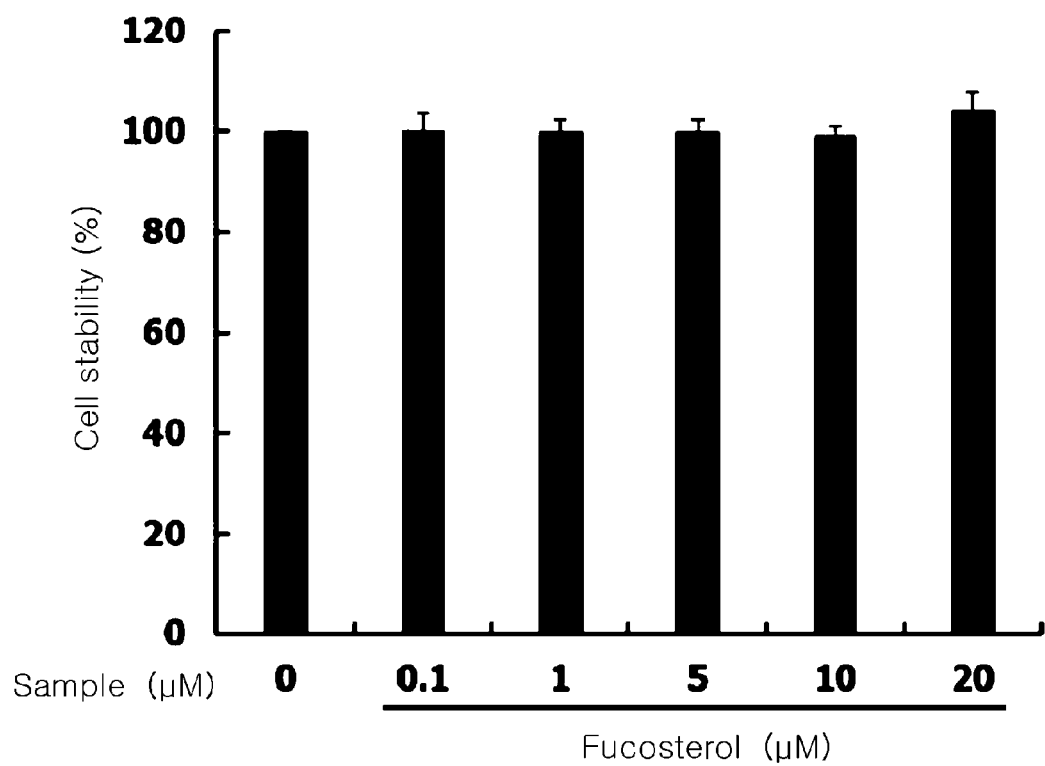
FIG. 1 is a result of measuring cytotoxicity according to a fucosterol treatment in B16F10 melanoma cells.

As illustrated in FIG. 1, the fucosterol was treated in the B16F10 melanoma cells and as a result, the cytotoxicity was not shown at a concentration of 0 to 20 μM.

Example 3 Inhibitory Effect on Melanin Generation According to Fucosterol Treatment in Melanoma Cells B16F10 melanoma cells were incubated in a DMEM medium including 10% fetal bovine serum and then added in a 6-well plate with $2.5 \times 10^5$ cell/mL (the final volume of 3 mL). After being incubated for 24 hrs, the medium was removed and fucosterol which was dissolved in the DMEM medium including 200 nM α-MSH was treated at 5, 10, and 20 μM concentrations, respectively. After 72 hrs, the incubated medium was removed from the 6-well plate and 0.25% trypsin-ethylenediaminetetraacetate (trypsin-EDTA) solution was treated to collect a cell pellet, and the cell pellet was transferred to a 1.5 mL tube and centrifuged for 10 min at 10,000 rpm to remove a supernatant. The obtained pellet was dried at 60° C. and added with 1N NaOH 100 μL to lyse melanin in the cells. This solution was diluted with phosphate buffered saline (PBS) and then the melanin content in a sample treatment group was calculated by measuring absorbance at 405 nm by an ELISA reader (Versa max, Sunnyvale, Calif., USA). In this case, cells without the fucosterol were set to a control group and the melanin generation degree was measured in the control group and cells treated with the fucosterol. According to Equation 1 below, the melanin content compared with the control group was calculated and the result was illustrated in FIG. 2.

Melanin content (%) compared with control group=absorbance of each test material/absorbance of control group×100  [Equation 1]

Figure 2:
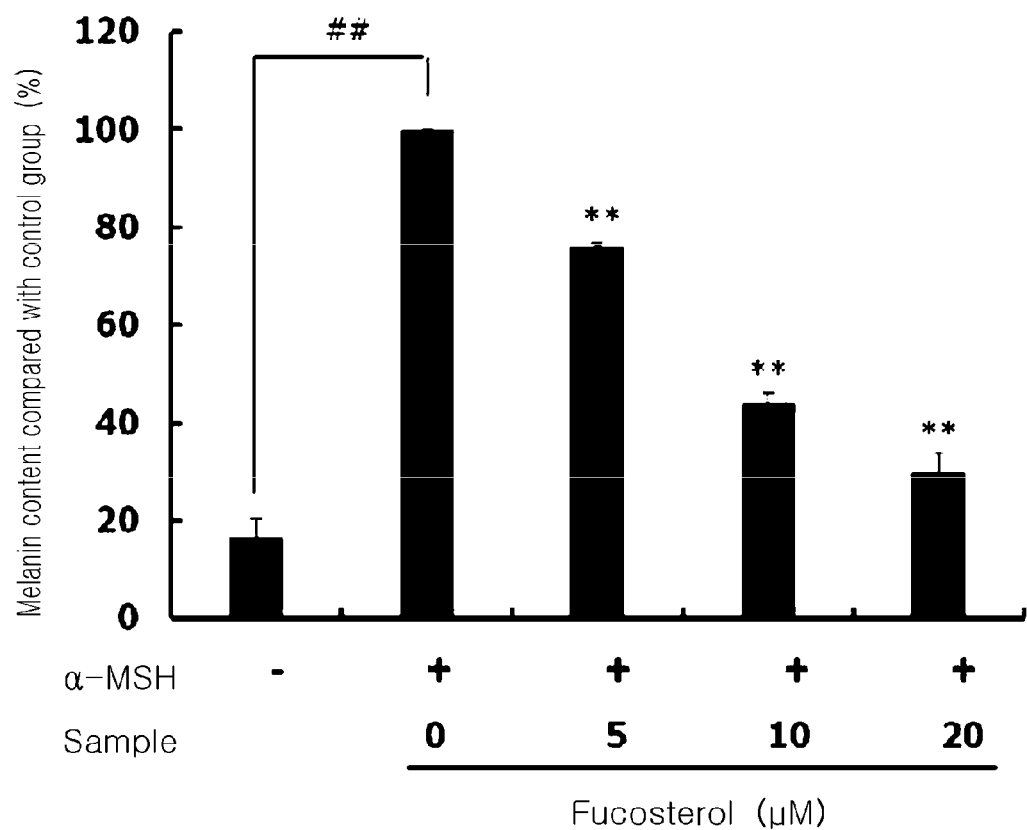
FIG. 2 is a result of quantitatively measuring an inhibitory effect on melanin generation according to the fucosterol treatment in the B16F10 melanoma cells.

As illustrated in FIG. 2, the fucosterol had a very excellent inhibitory effect on the melanin generation (**; P<0.01).

Example 4 Microscopic Observation of Inhibitory Effect on Melanin Generation According to Fucosterol Treatment in Melanoma Cells B16F10 melanoma cells were incubated in a DMEM medium including 10% fetal bovine serum and then added in a 6-well plate with $2.5×10^5$ cell/mL (the final volume of 3 mL). After being incubated for 24 hrs, the medium was removed and fucosterol which was dissolved in the DMEM medium including 200 nM α-MSH was treated at 5 and 20 µM of concentrations, respectively. After 72 hrs, the incubated medium was removed from the 6-well plate and the B16F10 melanoma cells were photographed by using a microscope (Olympus IX71 Model), and the result was illustrated in FIG. 3.

Figure 3:
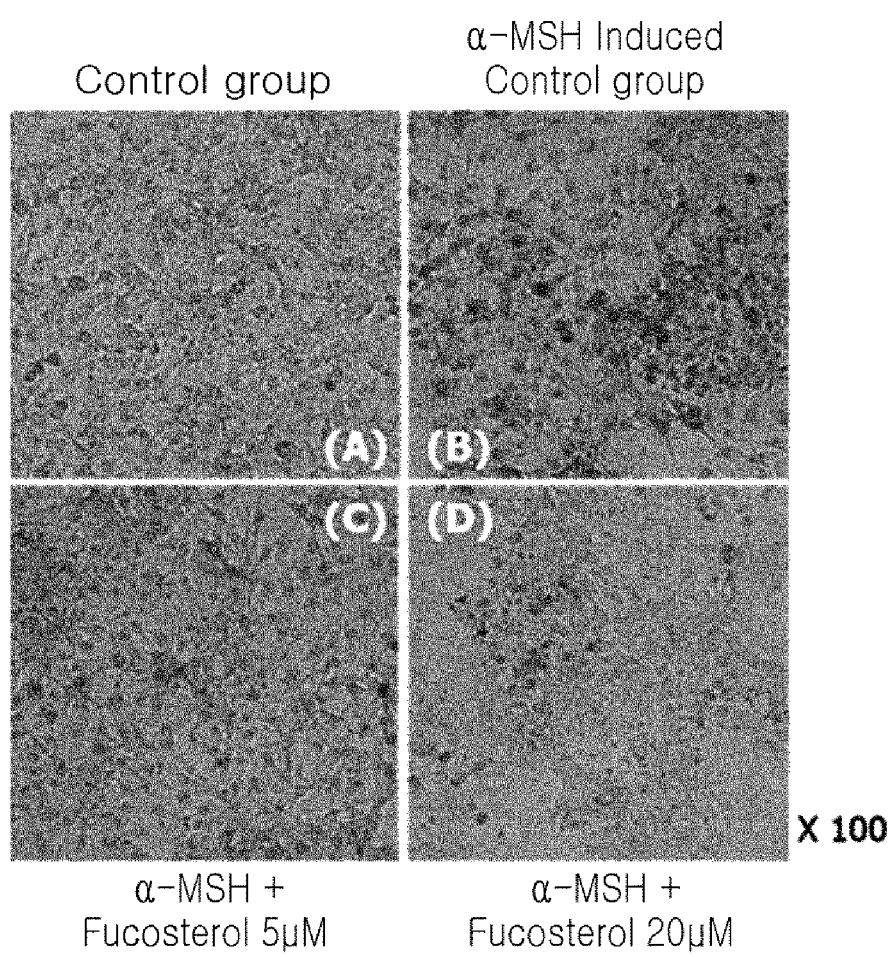
FIG. 3 is a result of observing an inhibitory effect on melanin generation by a microscope according to the fucosterol treatment in the B16F10 melanoma cells.

As illustrated in FIG. 3, the fucosterol largely inhibited the melanin generation of the B16F10 melanoma cells induced by the α-MSH.

Example 5 Inhibitory Effect on Tyrosinase Activity According to Fucosterol Treatment in Melanoma Cells B16F10 melanoma cells were incubated in a DMEM medium including 10% fetal bovine serum and then added in a 6-well plate with $2.5×10^5$ cell/mL (the final volume of 3 mL). After being incubated for 24 hrs, the medium was removed and fucosterol which was dissolved in the DMEM medium including 200 nM α-MSH was treated at 5, 10, and 20 µM concentrations, respectively. After 48 hrs, the incubated medium was removed from the 6-well plate and PBS including 1% Triton X-100 was added to collect the cells. The collected cells were centrifuged for 10 min and 150 µL of a supernatant was put in a 96-well plate and 50 µL of L-3,4-dihydroxyphenylalanine (L-DOPA) was added. With respect to an amount of dopachrome generated after incubated for 30 min at 37° C., absorbance was measured at 475 nm by using a microplate reader (Versa max, Sunnyvale, Calif., USA). In this case, cells without the fucosterol were set to a control group and the tyrosinase activity degree was measured in the control group and cells treated with the fucosterol. According to Equation 2 below, the tyrosinase activity compared with the control group was calculated and the result was illustrated in FIG. 4.

Tyrosinase activity (%) compared with control group=Reaction absorbance of each test material/Reaction absorbance of control group×100  [Equation 2]

Figure 4:
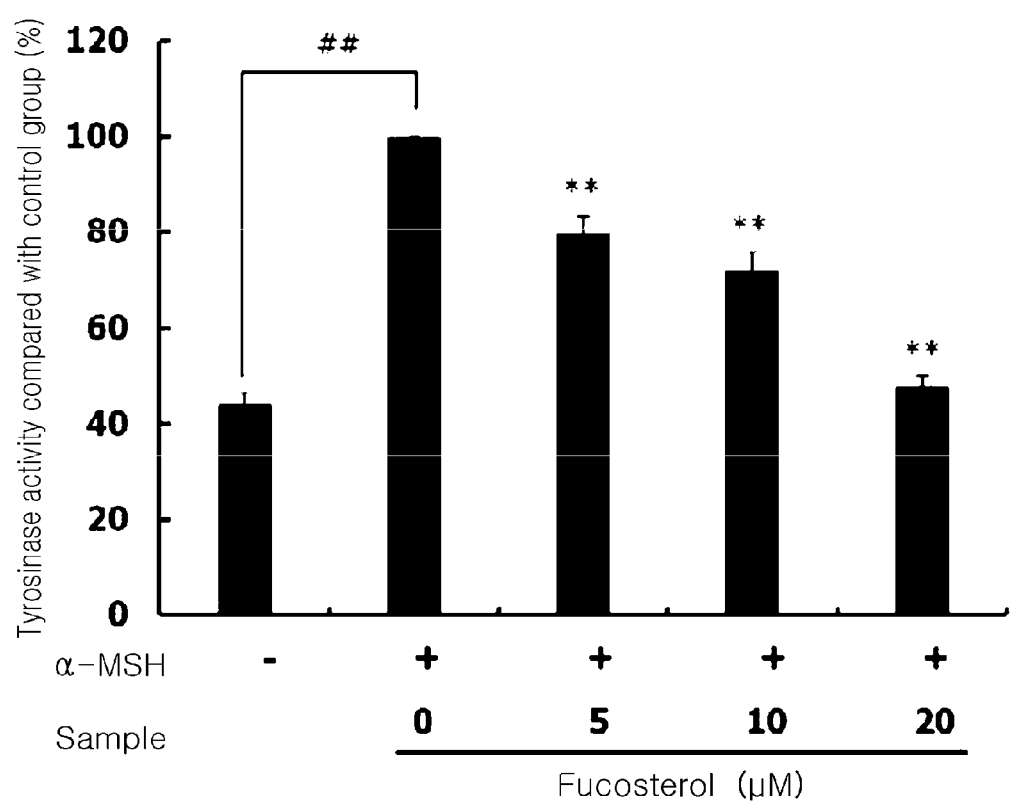
FIG. 4 is a result of measuring an inhibitory effect on tyrosinase activity according to the fucosterol treatment in the B16F10 melanoma cells.

As illustrated in FIG. 4, the fucosterol had a very excellent inhibitory effect on the tyrosinase activity (**: P<0.01).

Example 6 Reduction Effect on Tyrosinase Protein Expression According to Fucosterol Treatment in Melanoma Cells B16F10 melanoma cells were incubated in a DMEM medium including 10% fetal bovine serum and then added in a 6-well plate with $2.5×10^5$ cell/mL (the final volume of 3 mL). After being incubated for 24 hrs, the medium was removed and fucosterol which was dissolved in the DMEM medium including 200 nM α-MSH was treated at 5 and 20 µM of concentrations, respectively. The cells after 24 hrs were lysed with a NP40 buffer solution including proteinase inhibitor cocktail and the protein amount extracted from the cells was quantified by using a Bio-Rad protein assay dye (Bradford) reagent. The quantified protein was boiled for 5 min and isolated by electrophoresis with 10% SDS-PAGE to transfer the isolated proteins to a nitrocellular membrane. A primary antibody of tyrosinase was diluted in 2.5% bovine serum albumin at a ratio of 1:1000 and reacted with the protein transferred to the nitrocellular membrane for 20 hrs at room temperature. The primary antibody was reacted and the nitrocellular membrane was washed by using tris-buffer saline tween 20 (TBST) three times for 10 min. After washing, a secondary antibody (anti-goat horseradish) recognizing the primary antibody was diluted in 2.5% bovine serum albumin to be 1:5000 and reacted with the nitrocellular membrane for 2 hrs at room temperature and then washed three times by 10 min by using the TBST. A protein band was colored by using ECL western blotting detection reagents (Amersham, Tokyo, Japan) and the colored protein band was verified by using a G:BOX EF imaging system (Syngene, Cambridge, UK). As the measured result, the protein expression of tyrosinase was verified and the loading amount of the protein was constant by α-tubulin.

Figure 5:
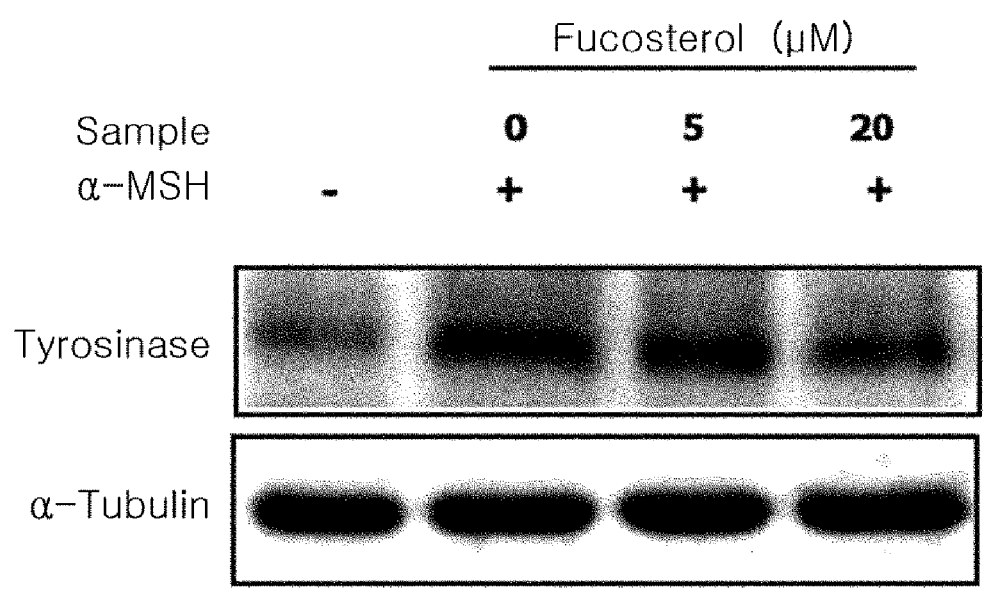
FIG. 5 is a result of measuring reduction in a protein expression level of tyrosinase according to the fucosterol treatment in the B16F10 melanoma cells.

As illustrated in FIG. 5, the fucosterol reduced the protein expression of tyrosinase as a melanin generation enzyme in the B16F10 melanoma cells.

Example 7 Reduction Effect on Protein Expression of Tyrosinase-Related TRP-1 and TRP-2 According to Fucosterol Treatment in Melanoma Cells B16F10 melanoma cells were incubated in a DMEM medium including 10% fetal bovine serum and then added in a 6-well plate with $2.5×10^5$ cell/mL (the final volume of 3 mL). After being incubated for 24 hrs, the medium was removed and fucosterol which was dissolved in the DMEM medium including 200 nM α-MSH was treated at 5 and 20 µM of concentrations, respectively. The cells after 24 hrs were lysed with a NP40 buffer solution including proteinase inhibitor cocktail and the protein amount extracted from the cells was quantified by using a Bradford reagent. The quantified protein was boiled for 5 min and isolated by electrophoresis with 10% SDS-PAGE to transfer the isolated proteins to a nitrocellular membrane. A primary antibody of TRP-1 and TRP-2 was diluted in 2.5% bovine serum albumin at a ratio of 1:1000 and reacted with the protein transferred to the nitrocellular membrane for 20 hrs at room temperature. The primary antibody was reacted and then the nitrocellular membrane was washed three times by using the TBST for 10 min. After washing, a secondary antibody (anti-goat horseradish) recognizing the primary antibody was diluted in 2.5% bovine serum albumin to be 1:5000 and reacted with the nitrocellular membrane for 2 hrs at room temperature and then washed three times by 10 min by using the TBST. A protein band was colored by using ECL western blotting detection reagents (Amersham, Tokyo, Japan) and the colored protein band was verified by using a G:BOX EF imaging system (Syngene, Cambridge, UK). As the measured result, the protein expression of TRP-1 and TRP-2 was verified and it was shown that the loading amount of the protein was constant by α-tubulin.

Figure 6:
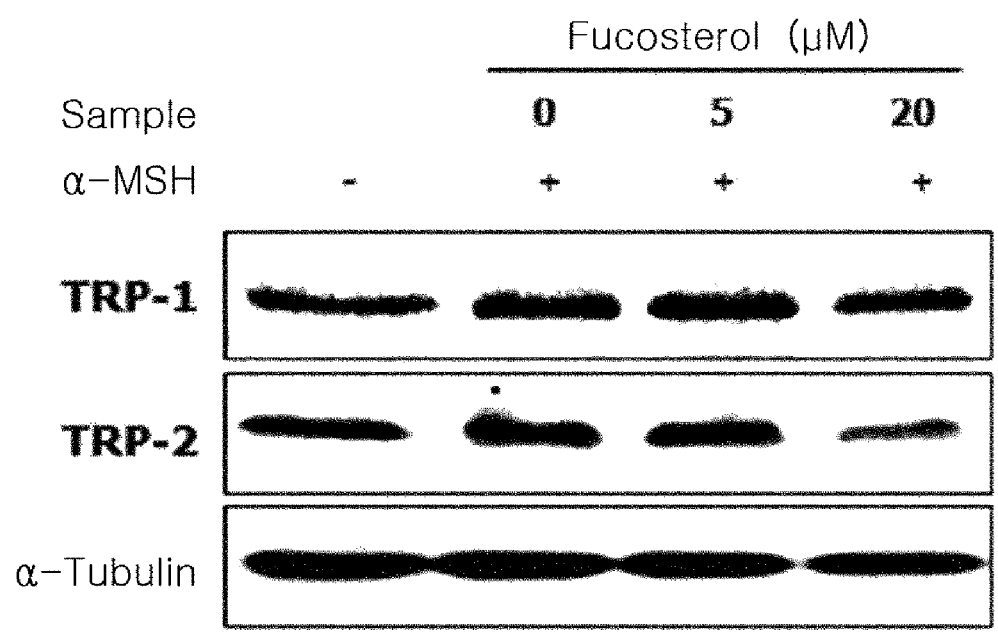
FIG. 6 is a result of measuring reduction in protein expression levels of TRP-1 and TRP-2 according to the fucosterol treatment in the B16F10 melanoma cells.

As illustrated in FIG. 6, the fucosterol reduced the protein expression of TRP-1 and TRP-2 as a melanin generation enzyme in the B16F10 melanoma cells.

Example 8 Reduction Effect on mRNA Expression of MITF According to Fucosterol Treatment in Melanoma Cells B16F10 melanoma cells were incubated in a DMEM medium including 10% fetal bovine serum and then added in a 6-well plate with $2.5 \times 10^5$ cell/mL (the final volume of 3 mL). After being incubated for 24 hrs, the medium was removed and fucosterol which was dissolved in the DMEM medium including 200 nM α-MSH was treated at 5 and 20 μM of concentrations, respectively. After 24 hrs, the total RNA was isolated by using a TRIzol reagent (Invitrogen, Carlsbad, Calif., USA). The isolated total RNAs were quantified by using a nano-drop (ND-1000). The quantified RNA was synthesized to cDNA by using reverse transcriptase and a PCR machine (Applied biosystems, Foster city, CA, USA) and then the PCR was performed with specific primers below.

```
GAPDH
                              (SEQ ID NO: 1)
Forward primer;    5'-ACCACAGTCCATGCCATCAC-3'

(SEQ ID NO: 2)
Reverse primer;    5'-CCACCCGAGCCACATCGCTC-3'

MITF
                              (SEQ ID NO: 3)
Forward primer;    5'-AGTCAACCTCTGAAGAGCA-3'

(SEQ ID NO: 4)
Reverse primer;    5'-CGTGTTCATACCTGGGCACT-3'
```

Figure 7:
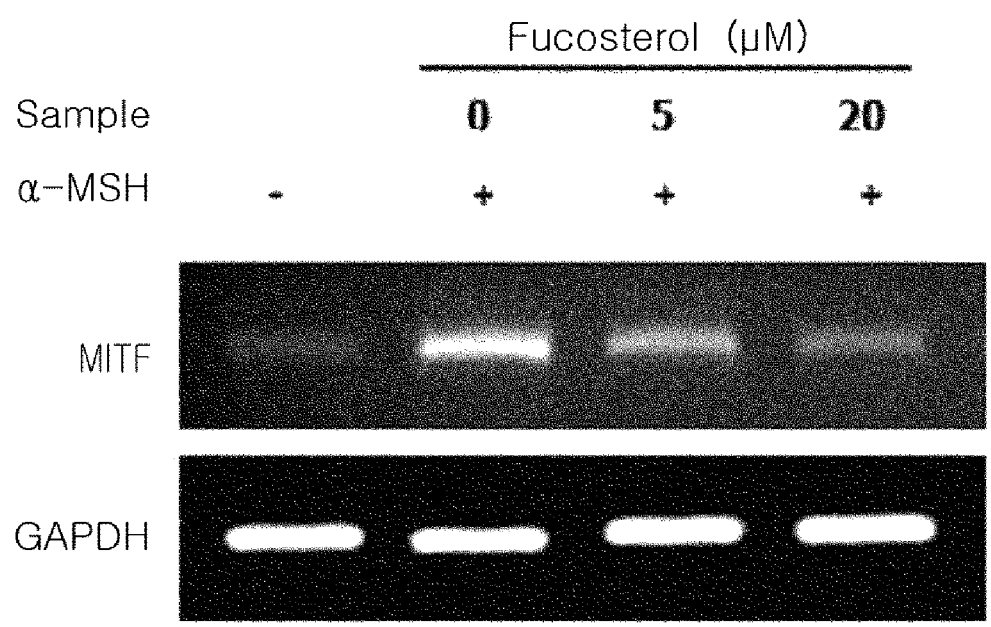
FIG. 7 is a result of measuring reduction in an mRNA expression level of MITF according to the fucosterol treatment in the B16F10 melanoma cells.

As the PCR result, the amplified cDNA was isolated with a 1.5% agarose gel by electrophoresis and cDNA bands were verified by using a G:BOX EF imaging system (Syngene, Cambridge, UK), and the result was illustrated in FIG. 7.

As illustrated in FIG. 7, the fucosterol reduced the mRNA amount of the the MITF regulating the protein expression of tyrosinase, TRP-1, and TRP-2 in the B16F10 melanoma cells.

Example 9 Effect on Cornified Envelope Formation According to Fucosterol Treatment in HaCaT Human Keratinocytes HaCaT human keratinocytes were incubated in a Dulbecco's Modified Eagle's Media (DMEM) medium including 10% fetal bovine serum and then put in a 6-well plate with $2 \times 10^5$ cell/ml (the final volume of 3 ml). After being incubated for 24 hrs, the medium was removed and fucosterol which was dissolved in the DMEM medium was treated at 5, 10, and 20 μM concentrations, respectively. After incubation for 96 hrs, the incubated medium was removed from the 6-well plate to collect a cell pellet, and the cell pellet was transferred to a 1.5 mL tube and centrifuged for 10 min at 10,000 rpm to remove a supernatant. The obtained pellet was added with a Tris buffer solution including 2% sodium dodecyl sulfate (SDS) and 20 mM dithiothreitol (DTT) and boiled, and the absorbance was measured at 340 nm to evaluate the effect on cornified envelope formation. According to Equation 1 below, the formation degree of the cornified envelope compared with the control group was calculated and the result was illustrated in FIG. 8.

$$\text{Cornified envelope formation amount (\%) compared with control group} = \text{absorbance of each test material/absorbance of control group} \times 100 \quad \text{[Equation 3]}$$

Figure 8:
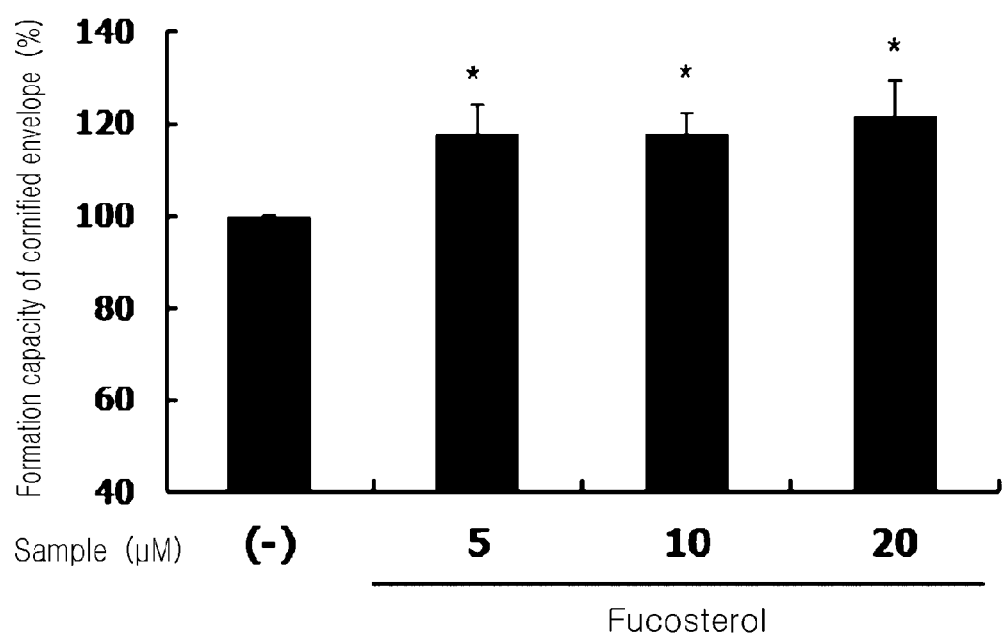
FIG. 8 is a result of measuring an effect on cornified envelope formation according to a fucosterol treatment in HaCaT human keratinocytes.

As illustrated in FIG. 8, it can be seen that the fucosterol has an excellent cornified envelope formation effect and an excellent moisturizing effect (*: p<0.05).

Example 10 Effect on Increase in mRNA Expression Levels of Loricrin, Involucrin, and Transglutaminase According to Fucosterol Treatment in HaCaT Human Keratinocytes HaCaT human keratinocytes were incubated in a Dulbecco's Modified Eagle's Media (DMEM) medium including 10% fetal bovine serum and then put in a 6-well plate with $2 \times 10^5$ cell/ml (the final volume of 3 ml). After being incubated for 24 hrs, the medium was removed and fucosterol which was dissolved in the DMEM medium was treated at 5, 10, and 20 μM concentrations, respectively. After 24 hrs, the total RNA was collected by using a TRIzol reagent (Invitrogen, Carlsbad, Calif., USA) and reverse-transcribed and then a reverse transcription-polymerase chain reaction (RT-PCR) analysis was performed below. First, for cDNA synthesis, the RNA was reverse-transcribed by reverse transcriptase. The RT-PCR was performed by specific primers below and the result was illustrated in FIG. 9.

```
GAPDH
                              (SEQ ID NO: 5)
Forward primer;    5'-TGACCTTGGCCAGGGGTGCT-3'

(SEQ ID NO: 6)
Reverse primer;    5'-CCACCCGAGCCACATCGCTC-3'

Loricrin
                              (SEQ ID NO: 7)
Forward primer;    5'-GGGTACCACGGAGGCGAAGGA-3'

(SEQ ID NO: 8)
Reverse primer;    5'-ACTGAGGCACTGGGGTTGGGA-3'

Involucrin
                              (SEQ ID NO: 9)
Forward primer;    5'-GGGGCAGCTGAAGCACCTGG-3'

(SEQ ID NO: 10)
Reverse primer;    5'-GAGACGGGCCACCTAGCGGA-3'

Transglutaminase
                              (SEQ ID NO: 11)
Forward primer;    5'CTTCCGTCTGCGCACCCCAG-3'

(SEQ ID NO: 12)
Reverse primer;    5'-AGGCACAAACGACTGGCGCA-3'
```

Figure 9:
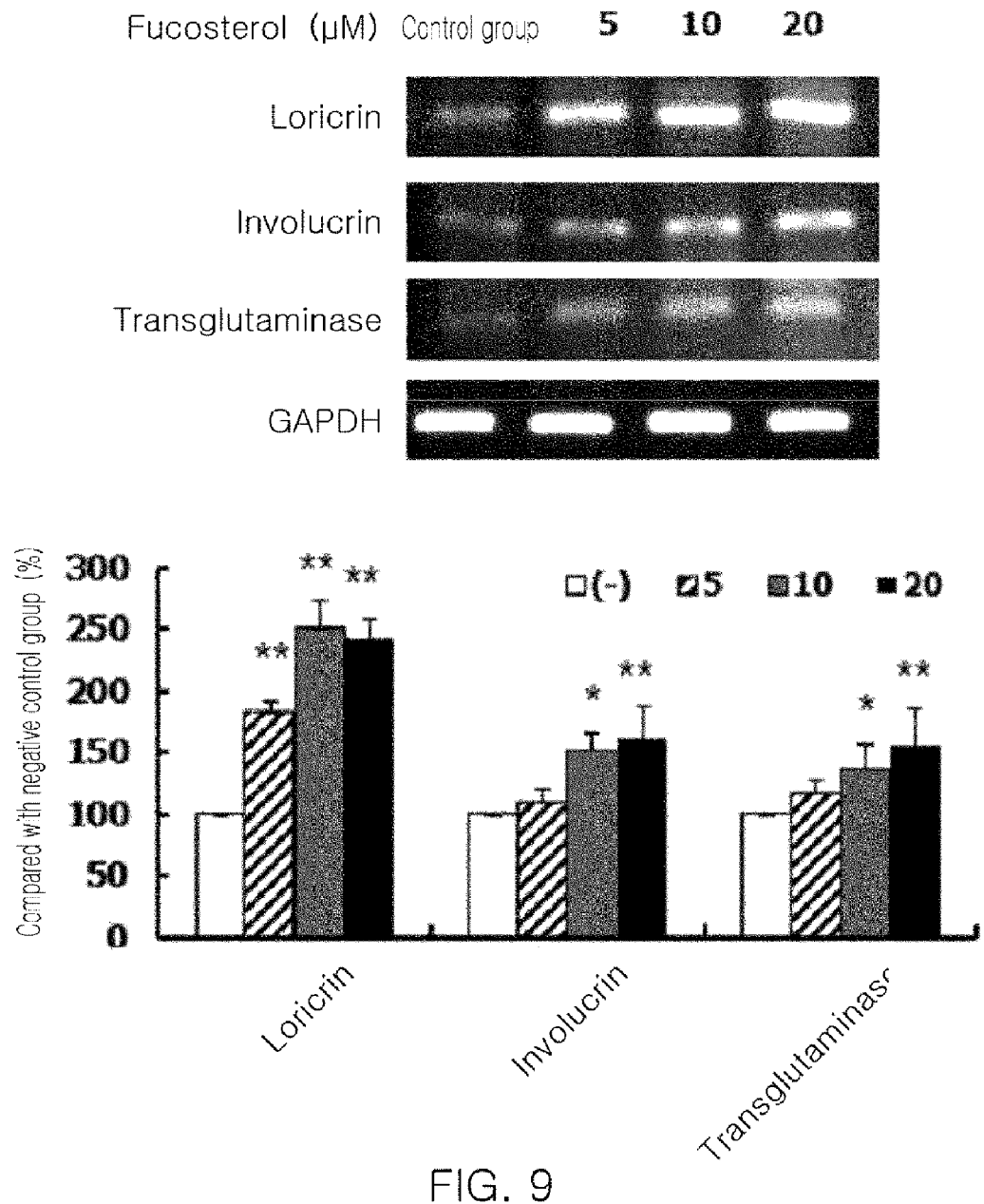
FIG. 9 is a result of measuring an increase in mRNA expression levels of differentiation factors, loricrin, involucrin, and transglutaminase according to the fucosterol treatment in the HaCaT human keratinocytes.

As illustrated in FIG. 9, it was verified that the mRNA expression of loricrin, involucrin, and transglutaminase according to the fucosterol treatment in the HaCaT human keratinocytes was increased. Therefore, it can be seen that the fucosterol has an excellent moisturizing effect by promoting the differentiation in the keratinocytes (*: p<0.05, **: p<0.01).

Example 11 Effect on Increase in Protein Expression Levels of Loricrin, Involucrin, and Transglutaminase According to Fucosterol Treatment in HaCaT Human Keratinocytes HaCaT human keratinocytes were incubated in a Dulbecco's Modified Eagle's Media (DMEM) medium including 10% fetal bovine serum and then put in a 6-well plate with $2\times10^5$ cell/ml (the final volume of 3 ml). After being incubated for 24 hrs, the medium was removed and fucosterol which was dissolved in the DMEM medium was treated at 5, 10, and 20 µM concentrations, respectively. After 24 hrs, the HaCaT human keratinocytes were lysed with a NP40 buffer solution including proteinase inhibitor cocktail. The protein amount extracted from the HaCaT human keratinocytes was quantified by using a Bradford method. The sample was boiled for 5 min and then the same amount of protein (20 g) was isolated by electrophoresis with 10% SDS-PAGE. The isolated proteins after electrophoresis were transferred to a nitrocellular membrane and western blot was performed. A primary antibody was reacted and the nitrocellular membrane was washed three times by using Tris-buffer saline tween20 (TBST) for 10 min. In this case, the kind and the dilution of the primary antibody used in the present invention is 1:1000. In a secondary antibody reaction, a secondary antibody was put in the membrane performing the primary antibody reaction and reacted for 2 hrs at room temperature. In this case, a dilution of the secondary antibody was 1:5000. Protein bands were colored by using ECL western blotting detection reagents (Amersham, Tokyo, Japan). The protein expression of loricrin, involucrin, and transglutaminase was verified and the loading amount of the protein was constant by α-tubulin.

Figure 10:
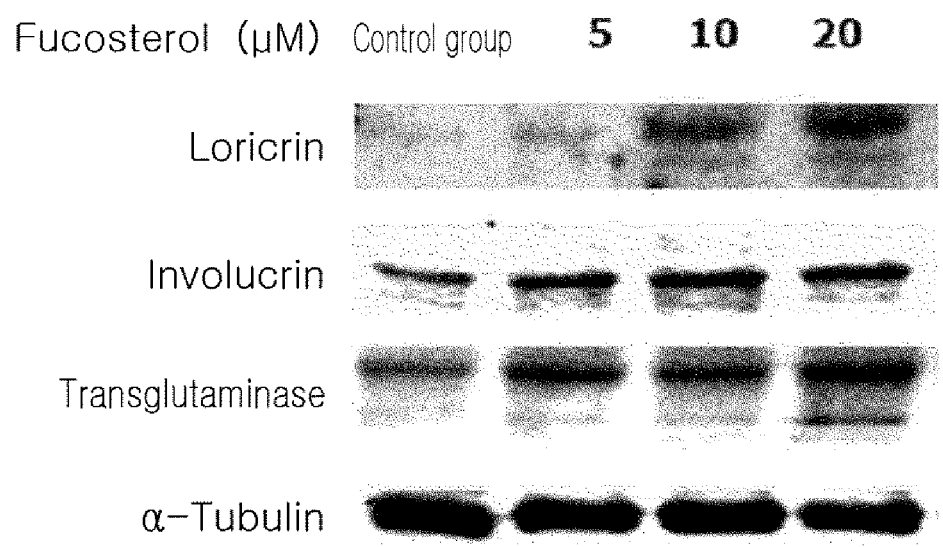
FIG. 10 is a result of measuring an increase in protein expression levels of differentiation factors, loricrin, involucrin, and transglutaminase according to the fucosterol treatment in the HaCaT human keratinocytes.

As illustrated in FIG. 10, it was verified that the protein expression of loricrin, involucrin, and transglutaminase according to the fucosterol treatment in the HaCaT human keratinocytes was increased. Therefore, it can be seen that the fucosterol has an excellent moisturizing effect by promoting the differentiation in the human keratinocytes.

Example 12 Effect on Increase in mRNA Expression Levels of Filaggrin and Caspase 14 According to Fucosterol Treatment in HaCaT Human Keratinocytes HaCaT human keratinocytes were incubated in a Dulbecco's Modified Eagle's Media (DMEM) medium including 10% fetal bovine serum and then put in a 6-well plate with $2\times10^5$ cell/ml (the final volume of 3 ml). After being incubated for 24 hrs, the medium was removed and fucosterol which was dissolved in the DMEM medium was treated at 5, 10, and 20 µM concentrations, respectively. After 24 hrs, the total RNA was collected by using a TRIzol reagent (Invitrogen, Carlsbad, Calif., USA) and reverse-transcribed and then a reverse transcription-polymerase chain reaction (RT-PCR) analysis was performed below. First, for cDNA synthesis, the RNA was reverse-transcribed by reverse transcriptase. The RT-PCR was performed by specific primers below and the result was illustrated in FIG. 11.

```
GAPDH
                                              (SEQ ID NO: 5)
Forward primer;    5'-TGACCTTGGCCAGGGGTGCT-3'

(SEQ ID NO: 6)
Reverse primer;    5'-CCACCCGAGCCACATCGCTC-3'

Filaggrin
                                             (SEQ ID NO: 13)
Forward primer;    5'-AGTGCACTCAGGGGGCTCACA-3'

(SEQ ID NO: 14)
Reverse primer;    5'-CCGGCTTGGCCGTAATGTGT-3'

Caspase 14
                                             (SEQ ID NO: 15)
Forward primer;    5'-CGGGACTCACAACCAAAGGA-3'

(SEQ ID NO: 16)
Reverse primer;    5'-GGGTCCCTTTGTTCTCCTCG-3'
```

Figure 11:
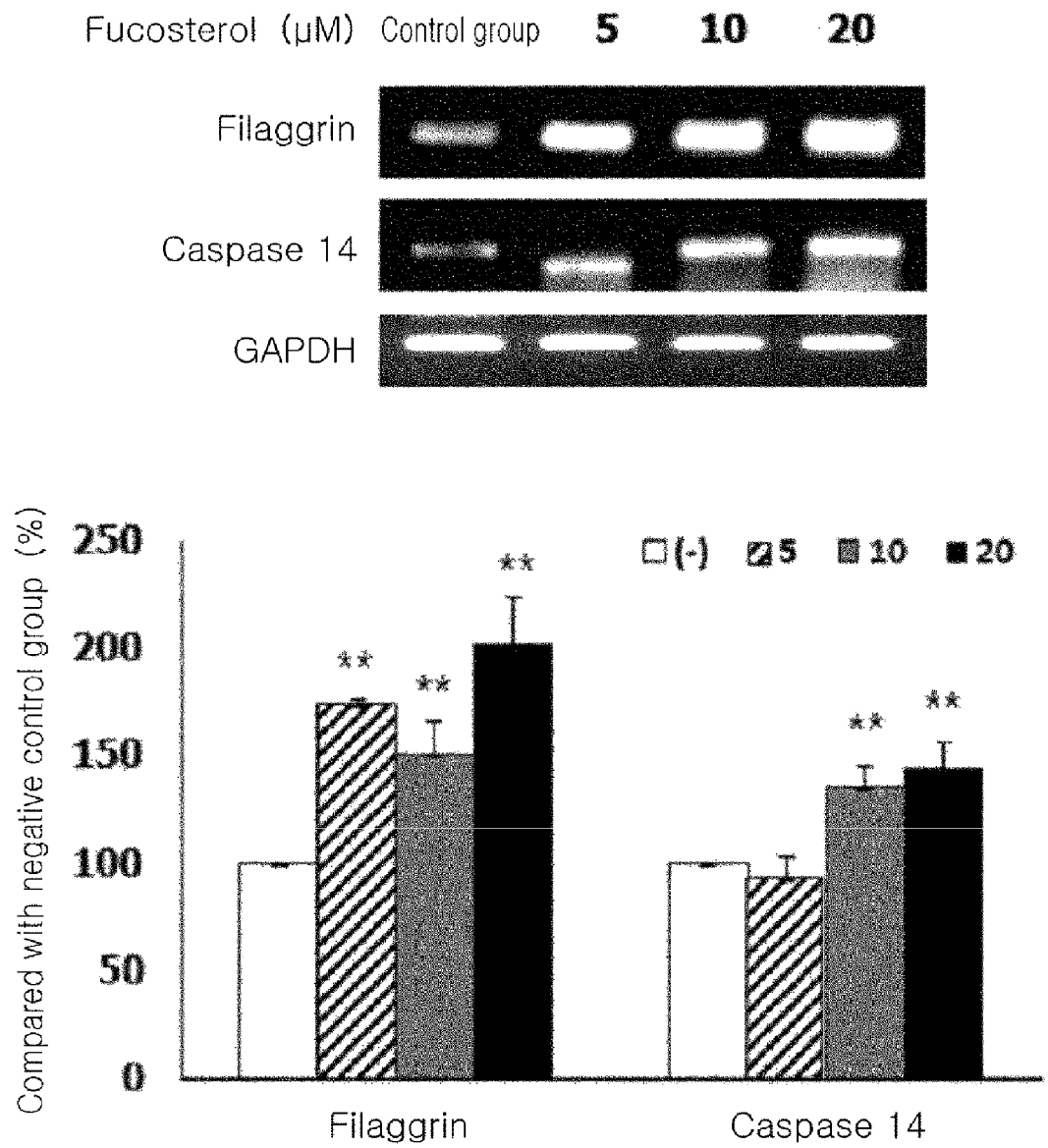
FIG. 11 is a result of measuring an increase in mRNA expression levels of filaggrin and caspase 14 according to the fucosterol treatment in the HaCaT human keratinocytes.

As illustrated in FIG. 11, it was verified that the mRNA expression of filaggrin and caspase 14 according to the fucosterol treatment in the HaCaT human keratinocytes was increased. Therefore, it can be seen that the fucosterol has an excellent moisturizing effect by generating natural moisturizing factors by an increase in expression levels of filaggrin and caspase 14 in the keratinocytes (*: $p<0.05$, **: $p<0.01$).

Example 13 Effect on Increase in Protein Expression Levels of Filaggrin and Caspase 14 According to Fucosterol Treatment in HaCaT Human Keratinocytes HaCaT human keratinocytes were incubated in a Dulbecco's Modified Eagle's Media (DMEM) medium including 10% fetal bovine serum and then put in a 6-well plate with $2\times10^5$ cell/ml (the final volume of 3 ml). After being incubated for 24 hrs, the medium was removed and fucosterol which was dissolved in the DMEM medium was treated at 5, 10, and 20 µM concentrations, respectively. After 24 hrs, the HaCaT human keratinocytes were lysed with a NP40 buffer solution including proteinase inhibitor cocktail. The protein amount extracted from the HaCaT human keratinocytes was quantified by using a Bradford method. The sample was boiled for 5 min and then the same amount of protein (20 g) was isolated by electrophoresis with 10% SDS-PAGE. The isolated proteins after electrophoresis were transferred to a nitrocellular membrane and western blot was performed. A primary antibody was reacted and the nitrocellular membrane was washed three times by using Tris-buffer saline tween20 (TBST) for 10 min. In this case, the kind and the dilution of the primary antibody used in the present invention is 1:1000. In a secondary antibody reaction, a secondary antibody was put in the membrane performing the primary antibody reaction and reacted for 2 hrs at room temperature. In this case, a dilution of the secondary antibody was 1:5000. Protein bands were colored by using ECL western blotting detection reagents (Amersham, Tokyo, Japan). The protein expression of filaggrin and caspase 14 was verified and it was shown that the loading amount of the protein was constant by α-tubulin.

Figure 12:
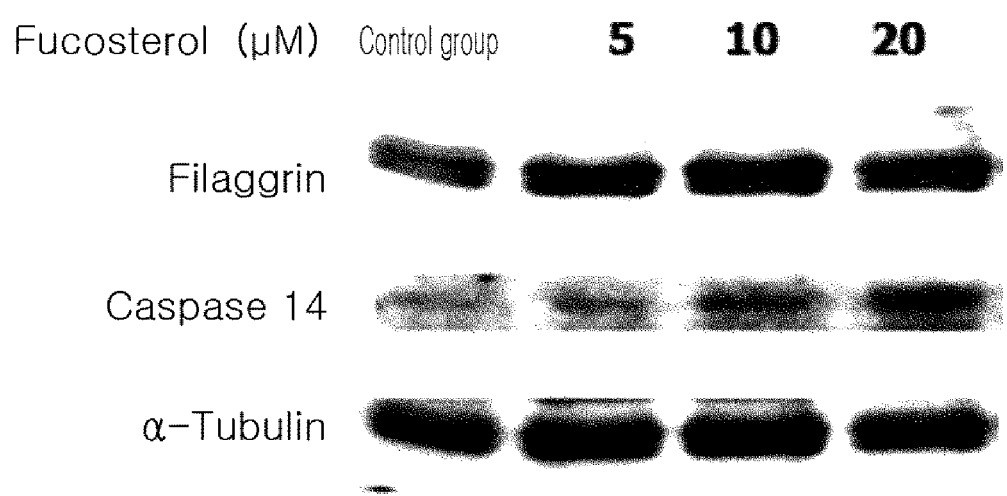
FIG. 12 is a result of measuring an increase in protein expression levels of filaggrin and caspase 14 according to the fucosterol treatment in the HaCaT human keratinocytes.

As illustrated in FIG. 12, it was verified that the protein expression of filaggrin and caspase 14 according to the fucosterol treatment in the HaCaT human keratinocytes was increased. Therefore, it can be seen that the fucosterol has an excellent moisturizing effect by generating natural moisturizing factors by an increase in expression levels of filaggrin and caspase 14 in the keratinocytes.

Formulation Examples of the cosmetics for skin whitening including the fucosterol according to the present invention as an active ingredient are described, but the present invention is not limited thereto but will be described in detail. The cosmetic compositions for skin whitening of Formulation Examples 1 to 6 having the fucosterol having the excellent skin whitening method according to composition ingredients and composition ratios below were prepared by a general method.

Formulation Example 1—Cosmetics

<1-1> Nutrition Lotion (Milky Lotion)

The nutrition lotion was prepared by using the fucosterol of Example 1 according to a general method with a formulation ratio of the nutrition lotion in Table 1 below.

TABLE 1

| Combined ingredients | Formulation Example 1-1 (wt %) |
|---|---|
| Fucosterol | 2.0 |
| Squalane | 5.0 |
| Wax | 4.0 |
| Polysorbate 60 | 1.5 |
| Sorbitan Sesquioleate | 1.5 |
| Liquid paraffin | 0.5 |
| Caprylic/Capric Triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, dye, flavoring | Suitable amount |
| Purified water | to 100 |

<1-2> Emollient (Skin Lotion)

The emollient was prepared by using the fucosterol of Example 1 according to a general method with a formulation ratio of the emollient in Table 2 below.

TABLE 2

| Combined ingredients | Formulation Example 1-2 (wt %) |
|---|---|
| Fucosterol | 2.0 |
| Glycerin | 3.0 |
| Butylene glycol | 2.0 |
| Propylene glycol | 2.0 |
| Carboxyvinyl polymer | 0.1 |
| PEG 12 nonylphenylether | 0.2 |
| Polysorbate 80 | 0.4 |
| Ethanol | 10.0 |
| Triethanolamine | 0.1 |
| Preservative, dye, flavoring | Suitable amount |
| Purified water | to 100 |

<1-3> Nourishing Cream

The nourishing cream was prepared by using the fucosterol of Example 1 according to a general method with a formulation ratio of the nourishing cream in Table 3 below.

TABLE 3

| Combined ingredients | Formulation Example 1-3 (wt %) |
|---|---|
| Fucosterol | 2.0 |
| Polysorbate 60 | 1.5 |
| Sorbitan Sesquioleate | 0.5 |
| PEG60 hydrogenated castor oil | 2.0 |
| Liquid paraffin | 10 |
| Squalane | 5.0 |
| Caprylic/Capric Triglyceride | 5.0 |
| Glycerin | 5.0 |
| Butylene glycol | 3.0 |
| Propylene glycol | 3.0 |
| Triethanolamine | 0.2 |
| Preservative | Suitable amount |
| Dye | Suitable amount |
| Flavoring | Suitable amount |
| Purified water | to 100 |

<1-4> Massage Cream

The massage cream was prepared by using the fucosterol of Example 1 according to a general method with a formulation ratio of the massage cream in Table 4 below.

TABLE 4

| Combined ingredients | Formulation Example 1-4 (wt %) |
|---|---|
| Fucosterol | 1.0 |
| Wax | 10.0 |
| Polysorbate 60 | 1.5 |
| PEG 60 hydrogenated castor oil | 2.0 |
| Sorbitan Sesquioleate | 0.8 |
| Liquid paraffin | 40.0 |
| Squalane | 5.0 |
| Caprylic/Capric Triglyceride | 4.0 |
| Glycerin | 5.0 |
| Butylene glycol | 3.0 |
| Propylene glycol | 3.0 |
| Triethanolamine | 0.2 |
| Preservative, dye, flavoring | Suitable amount |
| Purified water | to 100 |

<1-5> Pack

The pack was prepared by using the fucosterol of Example 1 according to a general method with a formulation ratio of the pack in Table 5 below.

TABLE 5

| Combined ingredients | Formulation Example 1-5 (wt %) |
|---|---|
| Fucosterol | 1.0 |
| Polyvinylalcohol | 13.0 |
| Sodium carboxymethyl cellulose | 0.2 |
| Glycerin | 5.0 |
| Allantoin | 0.1 |
| Ethanol | 6.0 |
| PEG 12 nonylphenylether | 0.3 |
| Polysorbate 60 | 0.3 |
| Preservative, dye, flavoring | Suitable amount |
| Purified water | to 100 |

<1-6> Gel

The gel was prepared by using the fucosterol of Example 1 according to a general method with a formulation ratio of the gel in Table 6 below.

TABLE 6

| Combined ingredients | Formulation Example 1-6 (wt %) |
|---|---|
| Fucosterol | 0.5 |
| Sodium ethylene diamine acetate | 0.05 |
| Glycerin | 5.0 |
| Carboxyvinyl polymer | 0.3 |
| Ethanol | 5.0 |
| PEG 60 hydrogenated castor oil | 0.5 |
| Triethanolamine | 0.3 |
| Preservative, dye, flavoring | Suitable amount |
| Purified water | to 100 |

Formulation Example 2—Food

<2-1> Preparation of Health Food

The health food may be prepared by mixing fucosterol 1000 mg of [Example 1], vitamin A acetate 70 μg, vitamin E 1.0 mg, vitamin B1 0.13 mg, vitamin B2 0.15 mg, vitamin B6 0.5 mg, vitamin B12 0.2 μg, vitamin C 10 mg, biotin 10

μg, nicotinic acid amide 1.7 mg, folic acid 50 μg, calcium pantothenate 0.5 mg, ferrous sulfate 1.75 mg, zinc oxide 0.82 mg, magnesium carbonate 25.3 mg, monopotassium phosphate 15 mg, dicalcium phosphate 55 mg, potassium citrate 90 mg, calcium carbonate 100 mg, and magnesium chloride 24.8 mg, and the combined ratio may be randomly modified. The ingredients are mixed according to a general method of preparing the health food to prepare granules and may be used in the preparation of a health food composition according to a general method.

<2-2> Preparation of Health Beverage

Fucosterol 1000 mg of [Example 1], citric acid 1000 mg, oligosaccharide 100 g, plum extract 2 g, and taurine 1 g are added with purified water, mixed according to a general method of preparing a health beverage of a total 900 mL, stirred and heated for about 1 hr at 85° C., and then the prepared solution is filtered, obtained in a sterilized container of 2 L, and refrigerated after sealing sterilization to be used for preparation of a health food composition.

<2-3> Chewing Gum

The chewing gum was prepared by mixing 0.1 wt % of the fucosterol of [Example 1] with gum base 20 wt %, sugar 76.9 wt %, flavoring 1 wt %, and water 2 wt % according to a general method.

<2-4> Candy

The candy was prepared by mixing 0.1 wt % of the fucosterol of [Example 1] with sugar 60 wt %, starch syrup 39.8 wt %, and flavoring 0.1 wt % according to a general method.

<2-5> Biscuit

The biscuit was prepared by mixing 0.1 wt % of the fucosterol of [Example 1] with first-class soft flour 25.59 wt %, first-class medium flour 22.22 wt %, refined sugar 4.80 wt %, salt 0.73 wt %, glucose 0.78 wt %, palm shortening 11.78 wt %, ammonium 1.54 wt %, sodium bicarbonate 0.17 wt %, sodium bisulfite 0.16 wt %, rice flour 1.45 wt %, vitamin B0.0001 wt %, milk flavor 0.04 wt %, water 20.6998 wt %, whole milk powder 1.16 wt %, substitute milk powder 0.29 wt %, moncalcium phosphate 0.03 wt %, spray salt 0.29 wt %, and spray oil 7.27 wt % according to a general method.

Formulation Example 3—Medicines

<3-1> Powder 50 mg of the fucosterol of [Example 1] and 2 g of crystalline cellulose were mixed and then filled in an airtight bag to prepare the powder according to a general method of preparing the powder.

<3-2> Tablet 50 mg of the fucosterol of [Example 1], 400 mg of crystalline cellulose, and 5 mg of magnesium stearate were mixed and then tableted to prepare the tablet according to a general method of preparing the tablet.

<3-3> Capsule 30 mg of the fucosterol of [Example 1], 100 mg of whey protein, 400 mg of crystalline cellulose, and 6 mg of magnesium stearate were mixed and then filled in a gelatin capsule to prepare the capsule according to a general method of preparing the capsule.

<3-4> Injection

According to a general method of preparing injections, an active ingredient was dissolved in distilled water for injection, pH was adjusted to about 7.5, and then 100 mg of the fucosterol of [Example 1], distilled water for injection, and a pH adjusting agent were mixed and filled in an ample of 2 mL and sterilized to prepare the injection.

INDUSTRIAL APPLICABILITY

The fucosterol of chemical formula 1 has an excellent whitening effect of inhibiting melanin generation and tyrosinase activity to be prepared as a cosmetic composition for whitening, a food composition, or a pharmaceutical composition, and thus industrial applicability is high.

Further, the fucosterol of chemical formula 1 has an excellent moisturizing function by forming dead skin cell membranes, promoting the differentiation of dead skin cells, and generating natural moisturization factors to be prepared as a cosmetic composition for moisturizing, a food composition, or a pharmaceutical composition, and thus industrial applicability is high.

The invention claimed is:

1. A method of improving skin whitening or moisturizing, the method comprising administrating a composition including fucosterol represented by the following Chemical Formula 1 as an active ingredient to a subject in need thereof, Chemical Formula 1

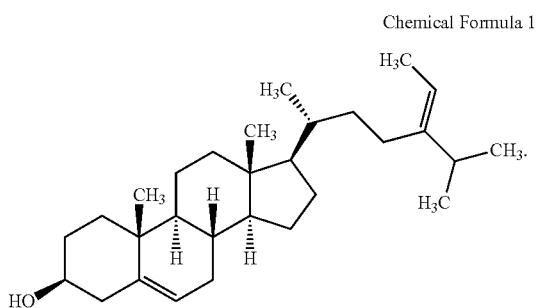

2. The method of claim 1, wherein the skin whitening is achieved by inhibiting a generation of melanin.

3. The method of claim 1, wherein the skin moisturizing is achieved by inhibiting an activity of tyrosinase or a protein expression of tyrosinase.

4. The method of claim 1, wherein the skin moisturizing is achieved by inhibiting a protein expression of tyrosinase related protein-1 or tyrosinase related protein-2, or a mRNA expression of microphthalmia transcription factor.

5. The method of claim 1, wherein the skin moisturizing is achieved by promoting a formation of a cornified envelope.

6. The method of claim 1, wherein the skin moisturizing is achieved by promoting a differentiation of corneous cells.

7. The method of claim 6, wherein the differentiation of corneous cells is promoted by increasing an expression of differentiation factors comprising loricrin, involucrin, and transglutaminase.

8. The method of claim 1, wherein the skin moisturizing is achieved by increasing an expression of filaggrin and caspase 14.

* * * * *